(12) United States Patent
Chee

(10) Patent No.: US 11,554,065 B2
(45) Date of Patent: Jan. 17, 2023

(54) PRESSURE RELIEF MATTRESS AND BODY PRESSURE MANAGEMENT SYSTEM THEREOF

(71) Applicant: AYZER SENSE TECHNOLOGY PTE. LTD., Singapore (SG)

(72) Inventor: Johnny Chee, Singapore (SG)

(73) Assignee: AYZER SENSE TECHNOLOGY PTE. LTD., Singapore (SG)

( * ) Notice: Subject to any disclaimer, the term of this patent is extended or adjusted under 35 U.S.C. 154(b) by 411 days.

(21) Appl. No.: 16/638,176

(22) PCT Filed: Aug. 3, 2018

(86) PCT No.: PCT/SG2018/050396
§ 371 (c)(1),
(2) Date: Feb. 11, 2020

(87) PCT Pub. No.: WO2019/035762
PCT Pub. Date: Feb. 21, 2019

(65) Prior Publication Data
US 2020/0360211 A1 Nov. 19, 2020

(30) Foreign Application Priority Data
Aug. 18, 2017 (SG) ............................ 10201706778S

(51) Int. Cl.
*A61G 7/057* (2006.01)
*A61B 5/00* (2006.01)

(52) U.S. Cl.
CPC .......... *A61G 7/05776* (2013.01); *A61B 5/002* (2013.01); *A61B 5/447* (2013.01);
(Continued)

(58) Field of Classification Search
CPC ...... A61B 2562/0247; A61B 2562/046; A61B 5/002; A61B 5/1036; A61B 5/447;
(Continued)

(56) References Cited

U.S. PATENT DOCUMENTS

| 2010/0101026 A1 | 4/2010 | Papaioannou |
| 2011/0308019 A1 | 12/2011 | Terawaki et al. |

(Continued)

FOREIGN PATENT DOCUMENTS

| CN | 101785613 A | 7/2010 |
| WO | 2016171695 A1 | 10/2016 |

OTHER PUBLICATIONS

Written Opinion and International Search Report of International Application No. PCT/SG2018/050396.

*Primary Examiner* — Toan N Pham
*Assistant Examiner* — Rajsheed O Black-Childress
(74) *Attorney, Agent, or Firm* — JCIP; Joseph G. Chu; Jeremy I. Maynard

(57) ABSTRACT

Disclosed herein is a pressure-relief mattress comprising: a plurality of inflatable bladders; a pressure sensor pad arranged to detect pressure exerted on a subject, the pressure sensor pad comprising a plurality of pressure sensor cells being arranged in a matrix with at least one row and at least one column; a pressure-sensing electronic unit electrically connected with the plurality of pressure sensor cells; and a pressure-control electronic unit communicatively connected with the pressure-sensing electronic unit; wherein the pressure-sensing electronic unit is configured for generating a measurement result indicative of a pressure exerted upon the subject at one or more of the pressure sensor cells, the pressure control electronic unit is configured for controlling operation of one or more of the inflatable bladders according to the pressure measurement result.

31 Claims, 8 Drawing Sheets

(52) U.S. Cl.
CPC .......... *A61B 5/6892* (2013.01); *A61B 5/7203* (2013.01); *A61B 5/746* (2013.01); *A61B 2562/0247* (2013.01); *A61B 2562/046* (2013.01); *A61G 2203/34* (2013.01)

(58) Field of Classification Search
CPC ..... A61B 5/6892; A61B 5/7203; A61B 5/746; A61G 2203/34; A61G 7/057; A61G 7/05776
See application file for complete search history.

(56) References Cited

U.S. PATENT DOCUMENTS

| | | |
|---|---|---|
| 2013/0283530 A1 | 10/2013 | Main et al. |
| 2015/0128354 A1 | 5/2015 | Greenstein et al. |
| 2016/0317370 A1 | 11/2016 | Evans et al. |
| 2017/0056264 A1 | 3/2017 | Chapin |

PRESSURE RELIEF MATTRESS AND BODY PRESSURE MANAGEMENT SYSTEM THEREOF

FIELD

The present invention relates to a pressure relief mattress and a body pressure management system.

BACKGROUND OF THE INVENTION

The following discussion of the background to the invention is intended to facilitate understanding of the present invention. However, it should be appreciated that the discussion is not an acknowledgment or admission that any of the material referred to was published, known or a part of the common general knowledge in any jurisdiction as at the priority date of the application.

Pressure ulcers or bedsores are lesions frequently developed when a localized area of soft tissue is compressed between a bony prominence and an external surface for a prolonged period of time.

Pressure ulcers are common in bedridden patients who suffered from coma, dementia, fractures, and strokes. Pressure ulcers can also occur in patients who are hospitalised for a week or longer. A pressure ulcer develops when an external high pressure exerted on a tissue reduces blood circulation in the tissue for a prolonged period. Once formed, the patients require nursing and medical care to recover. Pressure ulcers can last for prolonged period of time such as months or years, and they cause pain and in some cases, even death. Treatment of pressure ulcers is both difficult and expensive. Pressure ulcer management incurs additional costs beyond hospitalisation and can become an added burden to both the family and the medical institution.

Conventional methods to prevent pressure ulcers involve regular patient repositioning with the aid of pillows every two hours or other determined time intervals. Rotating patients regularly at pre-set intervals can be a labour-intensive task, requiring unrelenting diligence. Failure to rotate the patient within a stipulated time may aggravate and increase the risk of development of pressure ulcers. Moreover, the desired position is difficult to maintain as pillows tend to slip out.

Currently, pressure-relief mattress such as alternating-pressure mattresses or overlays may be used to help reduce the risk of developing pressure ulcers.

The alternating-pressure relief mattress provides a pressure relief via alternating high and low pressure locations on the mattress over all regions including those which are prone for pressure ulcers. The risk for developing pressure ulcers therefore remain. Moreover, an existing pressure ulcer will be aggravated every other alternate period.

A major limitation of the aforementioned prior art solutions is that pressure relief is performed randomly without knowing where the exact high-pressure region that could cause pressure ulcers can be, or whether the pressure relief is adequate, or whether repositioning the patient had created new high-pressure regions.

There exists a need to develop a pressure-relief system and a pressure relief mattress that ameliorates the drawbacks and at least in part.

SUMMARY OF THE INVENTION

According to an aspect of the invention, there is provided a pressure-relief mattress comprising a plurality of inflatable bladders, a pressure sensor pad arranged to detect pressure exerted on a subject, the pressure sensor pad comprising a plurality of pressure sensor cells being arranged in a matrix with at least one row and at least one column, a pressure-sensing electronic unit electrically connected with the plurality of pressure sensor cells, and a pressure-control electronic unit communicatively connected with the pressure-sensing electronic unit, wherein the pressure-sensing electronic unit is configured to selectively drive one or more of the pressure sensor cells for generating a pressure measurement result, the pressure-control electronic unit is configured to control operation of one or more of the inflatable bladders according to the pressure measurement result.

In some embodiments, the pressure sensor pad comprises a dielectric substrate, a plural rows of flexible conducting strips disposed on a first surface of the dielectric substrate, and a plural columns of flexible conducting strips disposed on a second surface of the dielectric substrate, the plural rows and columns of flexible conducting strips overlapping at a plurality of intersections to form the matrix of pressure sensor cells.

In some embodiments, the pressure relief mattress further comprises at least one fluid supply being operatively coupled to the inflatable bladders and being operatively connected with the pressure-control electronic unit.

In some embodiments, the dielectric substrate is made of a compressible dielectric material. In some embodiments, the compressible dielectric material is a polymeric foam.

In some embodiments, the pressure sensor pad comprises 120 to 650 pressure sensor cells.

In some embodiments, the pressure-sensing electronic unit is configured to control the pressure sensor cells using drive signals of a predetermined frequency range. In some embodiments, the frequency of the drive signals used by the pressure-sensing electronic unit to control the pressure sensor cells is in the range of 20 kHz to 200 kHz.

In some embodiments, the pressure-sensing electronic unit is configured to process electrical signals of a predetermined frequency range from the pressure sensor cells. In some embodiments, the frequency of the electrical signals from the pressure sensor cells is in the range of 20 kHz to 200 kHz.

In some embodiments, the pressure-sensing electronic unit comprises a sense amplifier for carrying out amplification of the electrical signals from the pressure sensor cells.

In some embodiments, the pressure sensor pad is configured to communicate with an external computing device. In some embodiments, the pressure sensor pad is configured to communicate with the external computing device via a wireless transmission unit.

In some embodiments, the wireless transmission unit comprises at least one Bluetooth transceiver. In some embodiments, the wireless transmission unit further comprises at least one ZIGBEE transceiver.

In some embodiments, the external computing device comprises a display unit, the display unit being configured to display the pressure measurement result in the form of a body pressure distribution map.

In some embodiments, the external computing device further comprises a control interface, the control interface being configured to switch between a plurality of operational modes.

In some embodiments, the pressure relief mattress further comprises a notification means for providing an alert to a caregiver.

In some embodiments, the notification means is configured to provide a notification to adjust the pressure of at least one of the plurality of inflatable bladders.

In some embodiments, the pressure relief mattress further comprises a timer, wherein the pressure relief mattress adjusts the pressure of at least one of the plurality of inflatable bladders at pre-determined time intervals.

In some embodiments, the plurality of pressure sensor cells can be also formed by a stretch-sensitive fabric, a piezo-resistive fabric, a plurality of force sensors, or a combination thereof.

According to another aspect of the invention, there is provided a system for managing a body pressure of one or more subjects comprising one or more pressure relief mattresses according to the first aspect of the invention, and one or more external computing devices in communication with the pressure relief mattresses, wherein the external computing device is configured to receive a pressure measurement result from one or more of the pressure relief mattresses for monitoring the pressure measurement result and for putting one or more of the pressure relief mattresses in various operational modes.

In some embodiments, the plurality of pressure relief mattresses are arranged in signal communication with each other via a wireless mesh network. In some embodiments, the wireless mesh network uses ZIGBEE wireless communication protocol.

According to another aspect of the invention, there is provided a method of managing a body pressure of a subject lying on a support surface comprising: measuring the body pressure at a plurality of locations on the support surface by using a pressure sensor pad having a matrix of pressure sensor cells, creating a pressure distribution map according to the body pressure measured at the plurality of locations, generating a pressure redistribution map according to the pressure distribution map, generating digital commands according to the pressure redistribution map, transmitting the digital commands to a pressure-redistribution layer having a plurality of inflatable bladders, and adjusting a pressure level in one or more inflatable bladders to a desired pressure level according to the digital commands.

According to another aspect of the invention, there is provided a process of manufacturing an pressure relief mattress comprising: providing an plurality of inflatable bladders arranged to form a pressure redistribution layer; providing a pressure-control electronic unit being affixed to the pressure redistribution layer; providing a pressure sensor pad above the inflatable bladders, the pressure sensor pad comprising a dielectric support layer, a plural rows of flexible conducting strips disposed on a top surface of the dielectric layer, and a plural columns of flexible conducting strips disposed on a bottom surface of the dielectric layer; providing a pressure-sensing electronic unit being affixed to the pressure sensor pad; and connecting the pressure-sensing electronic unit to the plural rows and columns of flexible conducting strips to form one or more electrical connections.

In some embodiments, the process of manufacturing the pressure relief mattress according further comprises forming a mattress overlay by enclosing the pressure redistribution layer and the pressure sensor pad with a protective cover.

In some embodiments, the process of manufacturing the pressure relief mattress further comprises: providing one or more soldering flux layers on the plural rows and columns of flexible conducting strips, applying a pre-determined temperature profile to the soldering flux layers, and connecting one or more electrical leads of the pressure-sensing electronic unit to the soldering flux layers.

According to another aspect of the invention, there is provided a control system for managing a body pressure of at least one subject comprising one or more pressure redistribution layers. Each one of the pressure redistribution WO 2019/035762
PCT/SG2018/050396 layer comprises a plurality of inflatable bladders, and a pressure-control electronic unit which comprises a communication module being configured to receive a pressure measurement result from a pressure sensor layer, and a controller module being operatively connected to one of more of the inflatable bladders, wherein the controller module is configured to identify one or more high-pressure regions according to the pressure measurement result, and generate one or more command streams for lowering the pressure at the identified high-pressure regions by adjusting pressure level in one or more of the inflatable bladders.

In some embodiments, the pressure redistribution layers of the control system are configured to connect with each other via a wireless mesh network. In some embodiments, the wireless mesh network uses ZIGBEE wireless communication protocol.

In some embodiments, the control system is arranged in communication with an external computing device for switching between a plurality of operational modes of one or more of the pressure redistribution layers.

In some embodiments, the control system further comprises a notification means for providing an alert to the caregiver. In some embodiments, the notification means is configured to provide a notification to adjust the pressure of at least one of the plurality of inflatable bladders.

In some embodiments, the control system comprises a timer, wherein the pressure redistribution layer adjusts the pressure of at least one of the inflatable bladders at pre-determined time intervals.

Other aspects of the invention will become apparent to those of ordinary skill in the art upon review of the following description of specific embodiments of the invention in conjunction with the accompanying drawings.

BRIEF DESCRIPTION OF THE DRAWINGS

The invention will now be described, by way of example only, with reference to the accompanying drawings, in which.

Figure 1:
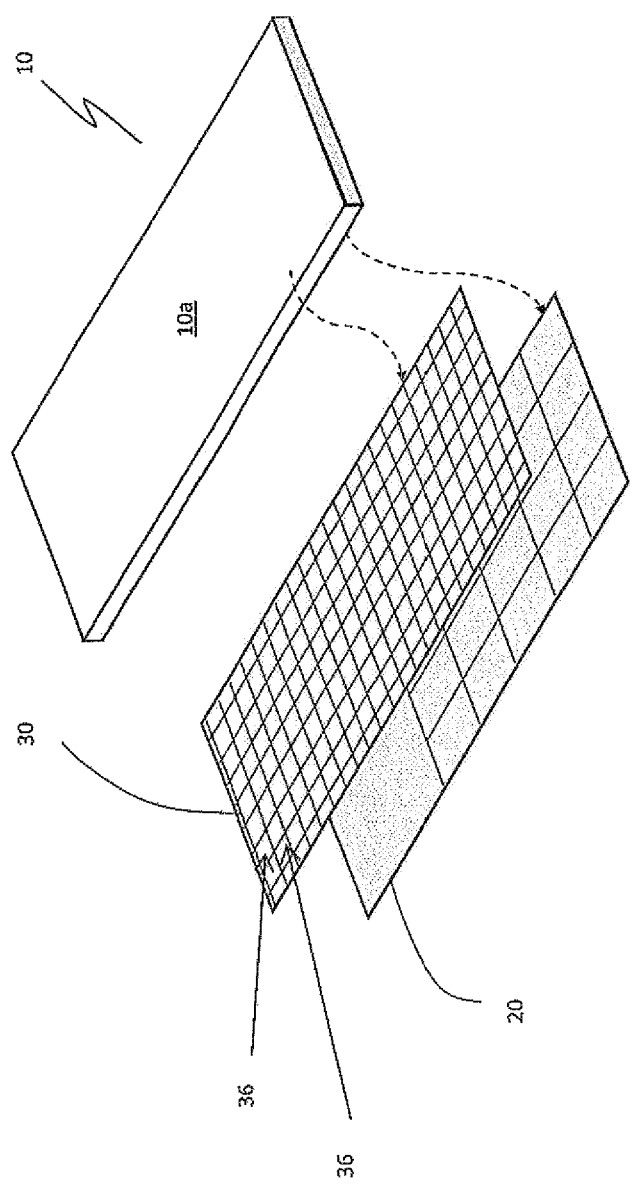
FIG. 1 shows an expanded view of a pressure relief mattress in accordance with an embodiment.

Other arrangements of the invention are possible and, consequently, the accompanying drawings are not to be understood as superseding the generality of the preceding description of the invention.

DETAILED DESCRIPTION

Particular embodiments of the present invention will now be described with reference to the accompany drawings. The terminology used herein is for the purpose of describing particular embodiments only and is not intended to limit the scope of the present invention. Other definitions for selected terms used herein may be found within the detailed description of the invention and apply throughout the description. Additionally, unless defined otherwise, all technical and scientific terms used herein have the same meanings as commonly understood by one ordinary skilled in the art to which the present invention belongs. Where possible, the same reference numerals are used throughout the figures for clarity and consistency.

Throughout the specification, unless the context requires otherwise, the word "comprise" or variations such as "comprises" or "comprising", will be understood to imply the inclusion of a stated integer or group of integers but not the exclusion of any other integer or group of integers.

Throughout the specification, unless the context requires otherwise, the word "include" or variations such as "includes" or "including", will be understood to imply the inclusion of a stated integer or group of integers but not the exclusion of any other integer or group of integers.

Throughout the specification, unless the context requires otherwise, the word "have" or variations such as "has" or "having", will be understood to imply the inclusion of a stated integer or group of integers but not the exclusion of any other integer or group of integers.

Throughout the specification, unless the context requires otherwise, the term "subject" includes but is not limited to a person (including a bed-bound patient) who is a user of the pressure relief mattress.

Throughout the specification, unless the context requires otherwise, the term "mattress" includes but is not limited to a structure used as a support surface for a subject, such as a fabric case filled with soft, firm, or resilient material such as spring(s), used for resting thereon.

Throughout the specification, unless the context requires otherwise, the term "fluid" includes but is not limited to a liquid such as water, and a gas such as air which is a mixture of gases.

Referring to the term "matrix", it includes, but is not limited to, a grid-like arrangement of elements, such as a rectangular array of elements in rows and columns. A matrix of elements can be treated as a single entity, and the elements within the matrix can be manipulated according to particular rules.

Referring to the term "micro-controller", it includes, but is not limited to, a microchip configured to execute operating logic that defines various control, management, and/or regulation functions. This operating logic can be in the form of software, firmware, and/or dedicated hardware, such as, a series of programmed instructions, code, electronic files, or commands using general purpose or special purpose programming languages, and/or a different form as would occur to those skilled in the art.

Referring to the term "computing device", it includes but it not limited to a computer laptop, cellphone, Smart phone, Personal Digital Assistant (or "PDA"), media player/reader, tablet personal computer, or any other processor-based device that is known in the art, including a desktop computer and/or computer workstation, as would occur to those skilled in the art.

In accordance with an embodiment of the invention and with reference to FIG. 1, there is a pressure relief mattress 10. The pressure relief mattress 10 comprises a plurality of inflatable bladders 20, a pressure sensor pad 30, a pressure-sensing electronic unit and a pressure-control electronic unit (not shown in FIG. 1). In some embodiments, the pressure relief mattress 10 may include an overlay. In some embodiments, the overlay includes or is in the form of a protective cover 10a enclosing both the plurality of bladders 20 and pressure sensor pad 30.

The plurality of inflatable bladders 20 may be arranged in an array format to support the entirety or at least a portion of the pressure sensor pad 30. The pressure sensor pad 30 may be positioned at a suitable location to sense one or more pressure points of a subject. For example, the pressure sensor pad 30 may be positioned above the array of inflatable bladders 20 to achieve compactness.

The pressure-sensing electronic unit is arranged in signal communication with the pressure sensor pad 30. It is appreciable that the signal communication can be achieved for example via a direct electrical connection or an indirect connection with the pressure sensor pad 30. A direct connection can be via electrical wires so that electrical signals (such as electrical voltage or electrical current) can be measured or obtained from the pressure sensor pad 30. The signal can be an analogue or a digital signal.

An indirect connection may be via a digital signal reading sent over wireless means to the pressure sensing electronic unit.

In some embodiments the pressure sensing electronic unit can be integrated wholly or in part with the pressure sensor pad 30, such as within a part/layer of the pressure sensor pad 30.

The pressure-control electronic unit can be integrated wholly or in part to the inflatable bladders 20, such as embedding into the inflatable bladders 20 or a part thereof. The pressure-control electronic unit is operatively arranged in signal communication with the pressure sensing electronic unit to receive an input signal from the pressure sensing electronic unit, the pressure sensing electronic unit operable to generate an output signal for controlling the inflatable bladders 20.

In various embodiments, a layer (e.g. upper layer) of the pressure sensor pad 30 and a layer (e.g. lower layer) of the inflatable bladders 20 are packed to form a mattress overlay with two inner layers. In various embodiments, the mattress overlay can include protective cover(s) 10a enclosing the mattress 10 against soiling.

One or more inflatable bladders 20 can be filled with air or other fluid. In various embodiments, the pressure relief mattress 10 further includes at least one fluid supply which is configured to inflate or deflate the inflatable bladders 20. Each inflatable bladder 20 may be individually pressurized by the fluid supply to a different pressure so as to vary the pressure exerted on different parts of the subject resting on the pressure relief mattress 10.

In various embodiments, at least one fluid supply is coupled to the inlet of the air bladders through one or more tubing and one or more solenoid valves. In some embodiments, the fluid supplies include an air pump that compresses air and supplies the compressed air to the inlet of one or more of the inflatable bladders via the tubing and the solenoid valves. It is within the scope of this disclosure for the fluid supply to supply various other gasses and/or liquids rather than air.

In various embodiments, the fluid supply includes a sensor arranged or positioned in the air pump or along the air pathway. The sensor is configured to detect the pressure of the compressed air being supplied to the air bladders.

In some embodiments, the fluid supply is integrated into the pressure relief mattress 10. In other embodiments, the fluid supply is coupled to other supporting structures in the vicinity of the pressure relief mattress 10. The supporting structures can include a bed frame.

Figure 2:
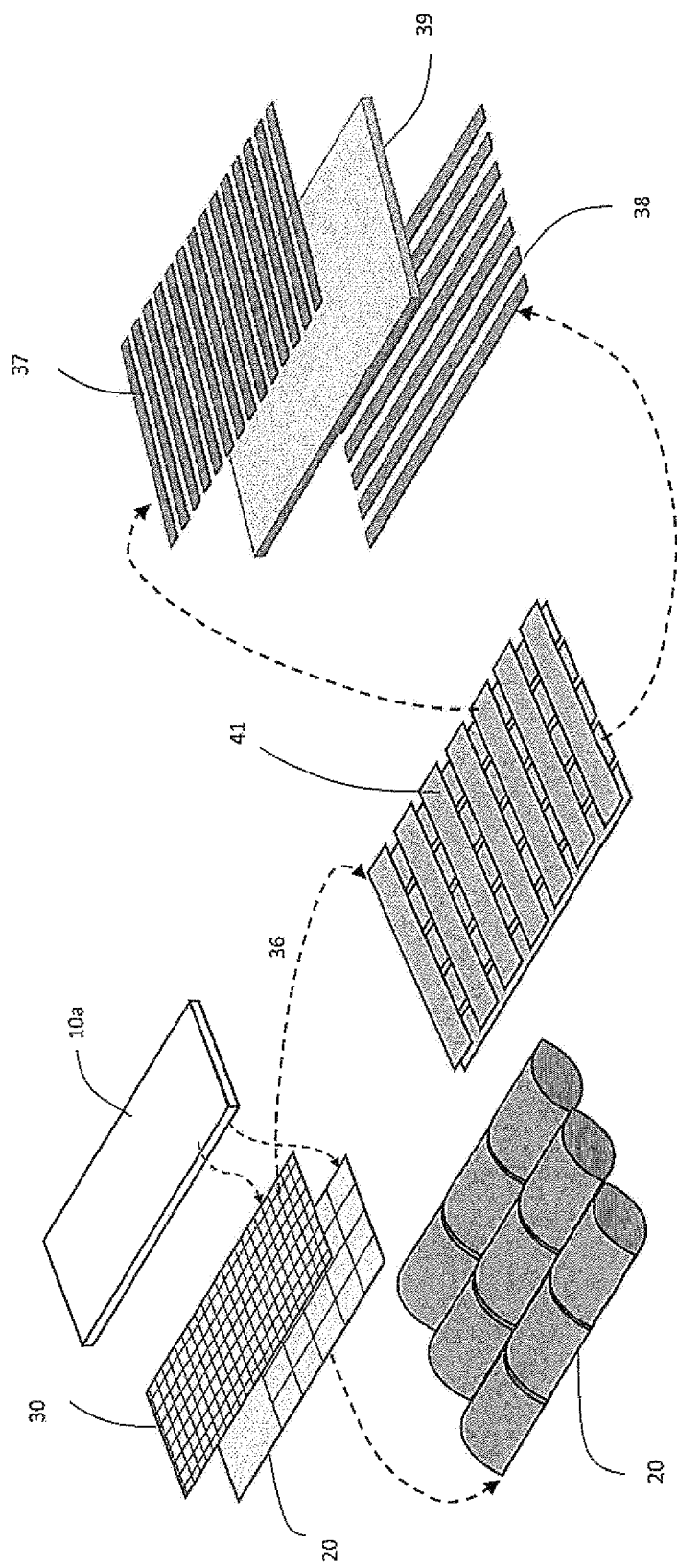
FIG. 2 shows an expanded view of a pressure relief mattress in accordance with an embodiment.

In various embodiments, the pressure sensor pad 30 is configured to measure pressure exerted on different part(s) of the subject resting on the pressure relief mattress 10. As shown in FIG. 1 and FIG. 2, the pressure sensor pad 30 includes a plurality of pressure sensor cells 36 arranged in multiple rows and multiple columns to form a matrix.

In various embodiments, one or more pressure sensor cells 36 in the matrix can be interconnected with one or more other pressure sensor cells 36 in the matrix. The pressure-sensing electronic unit and the pressure sensor cells 36 can be configured such that the pressure-sensing electronic unit can selectively drive one or more of the pressure sensor cells 36. In some embodiments, pressure sensor cells 36 placed in one row or in one column are electrically connected, such that one row or one column of pressure sensor cells in the matrix can be controlled by the pressure-sensing electronic unit as a group.

In various embodiments, neighbouring sensor cells 36 can be joined together or placed at a relatively small distance with each other, to form a continuous pressure-detecting surface. The gaps between neighbouring pressure sensor cells 36 are relatively small, such that interruptions or non-detecting area on the pressure-detecting surface formed by the pressure sensor cells is minimized. Advantageously, the arrangement of the pressure sensor cells 36 allows pressure exerted on a subject user to be detected along various directions continuously without minimum interruptions. The pressure detected at different pressure sensor cells 36 along different directions can be aggregated and processed by the pressure-sensing electronic unit into a body pressure map of the subject user.

Referring to the pressure sensor cells 36, each pressure sensor cell 36 in the matrix can include a capacitance sensor, which detects a strain or displacement due to a pressure applied onto the capacitance sensor.

By way of illustration, the capacitance sensor can be formed using a compressible dielectric material sandwiched by two conductive surfaces. A capacitance value of the capacitance sensor C can be calculated using the mathematical expression $$C = \epsilon \frac{A}{D}, \quad (1)$$

where $\epsilon$ is the dielectric constant of the dielectric material between the two conductive surfaces, A is the effective area of the conductive surface, and D is the effective separation between the two conductive surfaces. The spacing or the effective separation between the two conductive surfaces decreases when a pressure is applied directly on or over a surface adjacent to the capacitance sensor. Correspondingly, the capacitance changes in response to the applied pressure. By providing an oscillating voltage across the capacitance sensor of each pressure sensor cell 36 and by monitoring the electrical current produced by the pressure sensor cell 36, the capacitance of the capacitance sensor can be determined. Thus, where the properties of the capacitance sensor are known, the pressure applied upon the capacitance sensor at each pressure sensor cell 36 may be deduced from the electrical current measured. The electrical current is also referred to as capacitive current.

Figure 3:
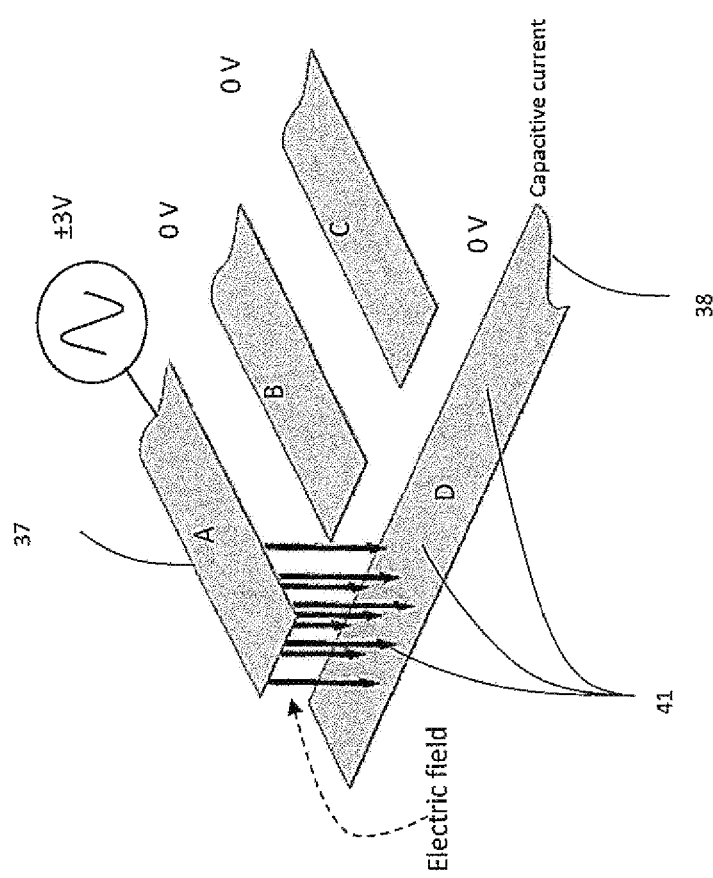
FIG. 3 illustrates a method of obtaining a pressure measurement result from a pressure relief mattress of FIG. 2.

In an embodiment as illustrated in FIG. 2 and FIG. 3, the pressure sensor pad includes one or more rows 37 and one or more columns 38 of conductive fabric strips sandwiching a compressible dielectric substrate 39. In other words, the one or more rows of conductive fabric strips 37 are provided on one surface of the compressible dielectric substrate 39, while the one or more columns of conductive fabric strips 38 are provided an opposite surface of the compressible dielectric substrate 39. The intersections 41 of the conductive fabric strips, which are separated by the compressible dielectric substrate 39, form the matrix of pressure sensor cells 36.

In an embodiment, the compressible dielectric substrate 39 is formed from a polymeric foam.

Using a compressible material such as a polymeric foam for the dielectric substrate effectively forms capacitance cells, of which the capacitance value can be varied by a pressure applied thereon. As illustrated and detailed in FIG. 3, three capacitance cells are formed between the sections of conductive strips A, B, C overlapping at each intersection with a conductive strip D. Pressing anywhere on the capacitance cells changes the spacing or effective separation between the conductive layers A, B, C and the conductive strip D, and consequently changing the capacitance value of the corresponding intersection. In addition, the pressure sensor pad which can be made of flexible conductive fabrics and compressible dielectric substrate as provided in the embodiment readily adapts or moulds onto the physical body geometry of the subject. Advantageously, the comfort of the subject user is improved.

The matrix of pressure sensor censor cells 36 is configured to sense pressure measurements/readings at different locations across the pressure sensor pad 30. The measurement results from numerous pressure sensor cells may be aggregated to form a map 52 showing a body pressure distribution of the subject resting on the pressure relief mattress 10 (see FIG. 5). As shown in FIG. 1 and FIG. 2, the pressure sensor pad 30 is formed by a relatively large number of pressure sensor cells or sensor points. The relatively large number of sensor points provides the benefit of improving data resolution of the pressure distribution map 52.

In some embodiments, the pressure sensor pad 30 comprises 120 to 650 pressure sensor cells 36. In some embodiments, the pressure sensor pad 30 comprises 140 to 648 pressure sensor cells 36. In other embodiments, the pressure sensor pad 30 comprises 160 to 250 pressure sensor cells 36. In yet other embodiments, the pressure sensor pad 30 comprises 160 to 300 pressure sensor cells 36.

Figure 4:
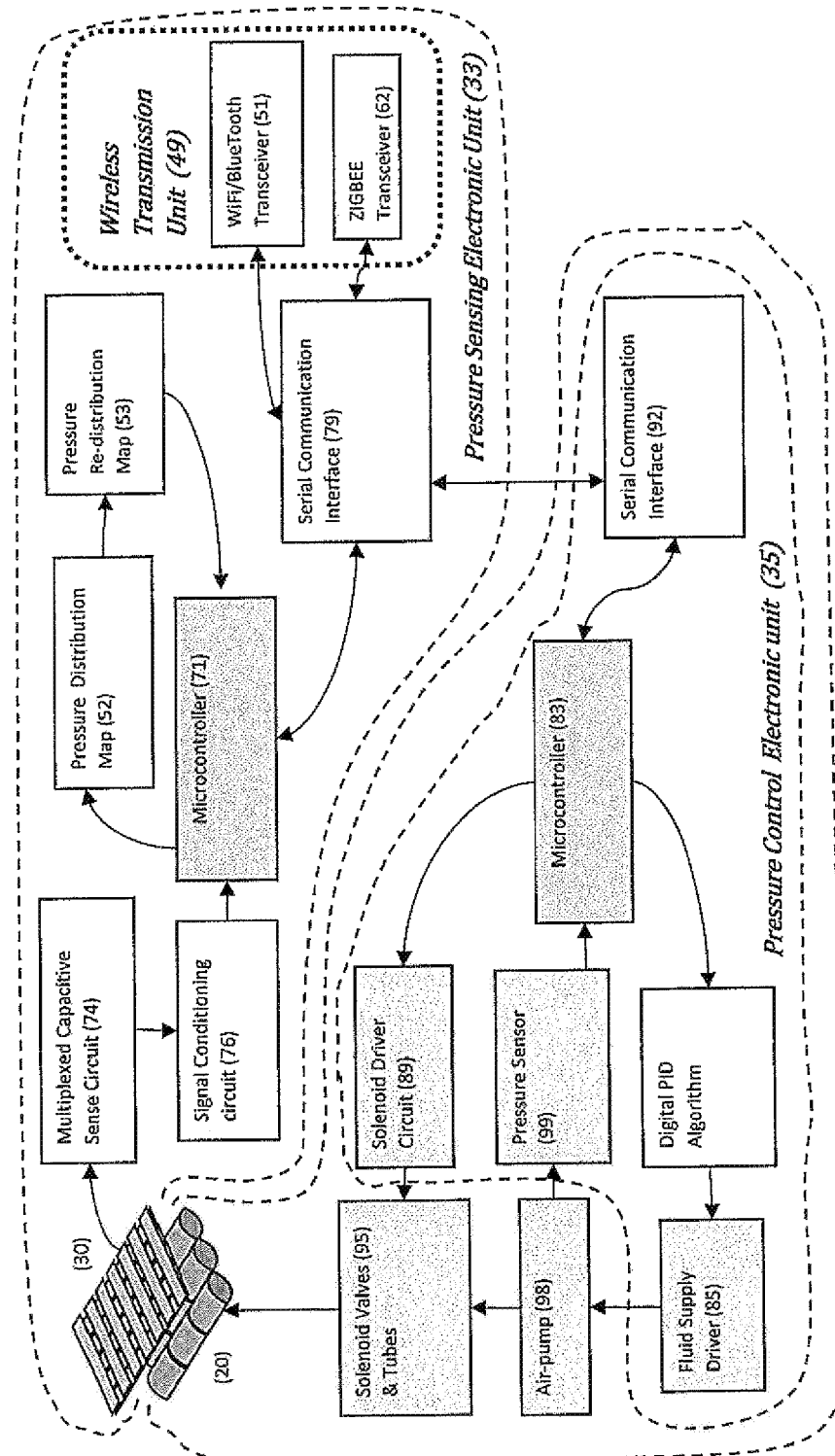
FIG. 4 illustrates a mode of operation of the pressure relief mattress of FIG. 1 and/or FIG. 2.

FIG. 4 shows a flow diagram, which provides an example of an operation sequence of the pressure relief mattress. The operation sequence is performed by the pressure-sensing electronic unit and the pressure-control electronic unit of the pressure relief mattress of FIG. 1 and FIG. 2 to achieve automatic body-pressure redistribution.

In various embodiments, the pressure sensing electronic unit 33 includes a first micro-controller 71, a multiplexed capacitive sense circuit 74, a signal conditioning circuit 76 and a first serial communication interface 79. The multiplexed capacitive sense circuit 74 is electrically connected to the pressure sensor pad 30, and is electrically connected to the signal conditioning circuit 76. The signal conditioning circuit 76 is electrically connected to the first micro-controller 71. The first serial communication interface 79 is also connected to the first micro-controller 71.

The first micro-controller 71 is configured to control operation of the other electronic components of the pressure-sensing electronic unit 33, including the multiplexed capacitive sense circuit 74, the signal conditioning circuit 76, and the first serial communication interface 79.

The first micro-controller 71 is configured to control the multiplexed capacitive sense circuit 74 for transmitting drive signals to one or more designated pressure sensor cells 36 in the pressure sensor pad 30. The designated pressure sensor cells 36 are put into a desired operational mode in accordance to the drive signals. For example, a designated pressure sensor cell 36 can be set to a pressure-sensing mode, whereby a voltage is applied across the pressure sensor cell and a capacitive current which relates to a pressure applied upon the designated sensor cell by the subject is measured from the pressure sensor cell.

The plurality of pressure sensor cells 36 of the pressure sensor pad 30 are arranged in a continuous matrix and are not isolated. In the pressure sensor pad 30 of the pressure relief mattress 10 of FIG. 2, the plurality of pressure sensor cells 36 are inter-connected via the plural rows 37 and columns 38 of conductive fabric strips.

As illustrated in FIG. 3, an electric field will form between any two conductive fabric strips, for example conductive fabric strip A and conductive fabric strip 13, whenever one of them is at a different potential from the other. In use, conductive fabric strip A is driven with a voltage that is fluctuating with respect to the voltage of conductive fabric strip D. The conductive fabric strip A is an active conductor for activating the functionality of the pressure sensor cell 36 at the intersection 41 formed between conductive fabric strip A and D.

The sensing conductive fabric strip D is configured to receive a current flow when the spacing between the conductive fabric strip A and conductive fabric strip D is changed, for example, by an external force or pressure. The current measured by the conductive fabric strip D is the capacitive current or the sensing current, indicative of the pressure applied above the pressure sensor cell formed at the intersection of conductive strip A and conductive strip D.

However, in a physical layout where there are multiple neighbouring conductors, the current received by sensing conductive strip D will be the sum of the capacitive current received from active conductive strip B and the capacitive current received from conductive fabric strips B and C, if there are any stray electrical field formed between the conductive strips B, C and the sensing conductive strip D.

In various embodiments, the first micro-controller 71 is configured to reduce measurement interference from the stray electric fields contributed by neighbouring conductive strips in vicinity of a selected pressure sensor cell. More specifically, the first micro-controller 71 drives a selected active conductive strip with an alternating voltage, forming an electrical potential with reference to a corresponding sensing conductive strip. The first micro-controller 71 also drives the neighbouring conductive strips with the same potential as the sensing conductive strip, such that only the capacitive current contributed by the active conductive strip is detected by the sensing conductive strip.

By way of an example and as shown in FIG. 3, if the sensing conductive strip D is kept at 0 V, the active conductive strip A is driven with an alternating voltage while the neighbouring conductors, such as conductive strips B and C, are also kept at 0 V. The capacitive current measured by the sensing conductive strip D therefore only comes from the active conductive strip A. In doing so, there will be no other electric fields except that from A to D. Similarly, capacitive current from other sensing conductive strips can be measured by treating their neighbouring conductive strips in a similar fashion, i.e. the other sensing conductive strips are maintained at the same potential as the sensing conductive strip.

Advantageously, only the electrical current contributed by the active conductive strip is measured, the interference from the stray electrical fields from the neighbouring conductive strips are eliminated or reduced to a negligible level. The signal-to-noise ratio (SNR) of the measurement result from the pressure sensor pad 30 is substantially enhanced.

In various embodiments, the multiplexed capacitive sense circuit 74 includes a plurality of analogue channels for receiving measurement results from the plurality of pressure sensor cells 36, and for converting the measurement results into one output electrical signal. In other words, the multiplexed capacitive sense circuit 74 can operate to combine measurement results from multiple pressure sensor cells 36 into one output electrical signal. This multiplexed output electrical signal is then transmitted to the signal conditioning circuit 76 and then to the first micro-controller 71.

The multiplexed capacitive sense circuit 74 provides the benefits of reducing the number of electronic components that are required to obtain the measurement results from the plurality of pressure sensor cells 36 to a small practical number.

The signal conditioning circuit 76 is configured to clean and process the electrical signals from the pressure sensor cells 36. In various embodiments, the signal conditioning circuit 76 includes a signal converter for converting the electrical signals received from the pressure sensor cells into digital signals. By way of an example, the signal converter can be an analog-to-digital converter (ADC). The output digital signals after signal conditioning are suitable for further processing by the first micro-controller 71.

In various embodiments, the signal conditioning circuit 76 includes a sense amplifier configured to carry out amplification of the electrical signals from the pressure sensor cells 36, such that the resolution of the electrical signals can be increased.

In various embodiments, the pressure sensor pad 30 and the pressure sensing electronic circuit 33 together are configured to minimize external interference from unwanted signals.

In use, any electrical/magnetic devices used in the vicinity of the pressure sensor pad and the pressure sensing electronic circuit can be a source of interfering signals or noise. By way of illustration and referring to the pressure relief mattress of FIG. 2, each of the conductive fabric strips may behave as a receiving antenna for all electromagnetic signals generated by other electrical sources in the vicinity, such as those from power lines of the pressure relief mattress or from other electronic devices. These unwanted electromagnetic signals appear as noise in the measurement of the pressure sensor cells 36.

In various embodiments, the pressure sensing electronic unit 33 is configured to operate without being interfered by the unwanted electromagnetic signals. The first micro-controller 71 of the pressure sensing electronic circuit 33 is configured to transmit drive signals to the pressure sensor cells 36 within a pre-determined signal frequency range, or within a narrow band of signal frequency (i.e. akin to a bandpass filter), which excludes substantial amount of the unwanted signals outside the narrow band. In some embodiments, the first micro-controller 71 is configured to transmit drive signals to the pressure sensor cells 36 with a frequency in the range between 20 kHz and 200 kHz.

Further, the pressure-sensing electronic unit 33 is configured to analyse electrical signals from the pressure sensor cells 36 within a pre-determined signal frequency range, or within a narrow band of signal frequency. In various embodiments, the sense amplifier of the signal conditioning circuit 76 is configured to selectively process and amplify electrical signals within a pre-determined signal frequency range, or within a narrow band of signal frequencies. In some embodiments, the sense amplifier is configured to process and amplify electrical signals with a frequency range between 20 kHz and 200 kHz.

The electrical signals within the pre-determined signal frequency range contain valid information indicative of the measurement result from the pressure sensor cells 36. In other words, unwanted electrical signals outside the pre-determined signal frequency range, which can be a noise to the measurement result, are rejected and are not amplified by the sense amplifier.

Within the pre-determined signal frequency range, the measurement result, in the form of a capacitive current, generated by the pressure sensor pad and detected by the pressure-sensing electronic unit is large enough for good signal-to-noise (SNR) rejection, and yet the frequency of the drive signals used is not too high to generate any significant level of electromagnetic radiation. Advantageously, the enhanced signal-to-noise ratio provides a more accurate pressure measurement result.

In various embodiments, a modulator can be coupled to the multiplexed sensing circuit 74, which is adapted to perform an on-off modulation of the drive signals to be transmitted to one or more of the pressure sensor cells 36 and/or the electrical signals indicative of the measurement results received from the pressure sensor cells 36. In use, multiplexing an oscillating electrical signal generates a large number of accompanying harmonics, causing the information embedded in the oscillating electrical signals to be distorted during extraction. The modulator provides a means to regulate the waveform of the output electrical signals, by adjusting the gain or feedback fraction of the oscillating electrical signals. During the process of multiplexing and/or de-multiplexing and while no measurement result is taken from pressure sensor cells, the modulator operates to set the drive signals and/or the electrical signal to zero. When the multiplexed sensing circuit 74 measures the capacitive current from the pressure sensor cells 36, the modulator then operates to provide a stable oscillation of the drive signals and/or the output electrical signals. Advantageously, the impact of the accompanying harmonics caused by the oscillating electrical signals is minimized, and the signal-to-noise ratio of the measurement result from the pressure sensor cells 36 is further enhanced.

Referring back to FIG. 4, the measurement result from the plurality of pressure sensor cells 36, after signal processing by the multiplexed sensing circuit 74 and signal conditioning circuit 76, is then transmitted to the first micro-controller 71. The first microcontroller 71 then processes and transmits out digital signals as a result of the processing. Signal transmission may be wireless or via data cables according to requirements.

In various embodiments, the first micro-controller 71 is configured to perform map extraction based on the measurement results from the plurality of pressure sensor cells 36. In detail and by way of illustration, the first micro-controller 71 may be configured to interpret the measured capacitive current values and to analyse the data to determine which pressure sensor cells have pressure applied to them. The interpretation may be performed by consulting a lookup table stored in the micro-controller 71, which maps capacitive current values to pressure values, often cited as units of millimetres of mercury (mm Hg), as commonly used in medical settings, or in scientific units such as kilo pascal (kPa). The pressure values from multiple pressure sensor cells 36 are then aggregated to form a pressure profile 52, which is also known as a pressure distribution map 52. The first micro-controller 71 may be further configured to store data of one or more pressure distribution maps 52 per subject formed over time. From one or more of the pressure distribution maps 52, high-pressure points or high-pressure regions are identified.

The first micro-controller 71 is also configured to generate a command stream for adjusting the body-weight support of the subject lying on the pressure relief mattress 10 based on the high-pressure points or high-pressure regions identified from the pressure distribution map 52. In various embodiments, the first micro-controller 71 operates to perform digital signal processing to extract a plurality of strategic measurement parameters from the pressure distribution map 52. One or more algorithms are applied on the measurement parameters to compute a pressure redistribution map 53. In various embodiments, the one or more algorithms involve identifying high-pressure regions by aggregating readings of pressure above a threshold value by their spatial locations and subsequently generating the pressure redistribution map 53.

The pressure redistribution map 53 is then converted into a command stream by the first micro-controller 71 for sending to the pressure-control electronic circuit 35. The command stream being converted from the pressure redistribution map 53 is also referred to as a pressure redistribution command.

In various embodiments, different algorithms may be applied to form the command streams to generate different pressure relief patterns while ensuring that no high-pressure points occur on the subject's body.

In various embodiments, the pressure-control electronic unit 35 includes a second micro-controller 83, a fluid supply driver circuit 85, a solenoid valve driver circuit 89, and a second serial communication interface 92. The second serial communication interface 92 is connected to the second micro-controller 83, and is communicatively coupled with the first communication interface 79. The second micro-controller 83 is also operatively connected with the fluid supply driver circuit 85 and the solenoid valve driver circuit 89.

The second serial communication interface 92 at the pressure-sensing electronic unit 35 and the first communication interface 79 at the pressure-control electronic unit 33 are configured to establish a communication or data transmission means between the pressure-sensing electronic unit 33 and the pressure-control electronic unit 35. The command stream for adjusting the body-weight support of the subject is transmitted from the pressure-sensing electronic unit 33 to the second micro-controller 83 of the pressure-control electronic unit 35, via the two serial communication interfaces 79, 92. It should be understood that use of other data transmission means are also contemplated.

The second micro-controller 83 provided in the pressure-control electronic unit 35 is configured to interpret the command stream and to perform pressure-control of the different inflatable bladders 20 according to the command stream.

In use, the second micro-controller 83 transmits drive signals to the solenoid driver circuit 89, which is configured to control the operation of the solenoid valves 95 at the inlets of the different inflatable bladders 20. In addition, the second micro-controller 83 activates the solenoid driver circuit 89 to select one or more inflatable bladders 20 to be inflated or deflated. The second micro-controller 83 also transmit drive signals to the fluid supply driver 85, which in turn provides power to an air pump 98 to supply a compressed air or gas to the inflatable bladders 20. According to the drive signals, the inflatable bladders 20 are individually pressurized to a desired pressure level.

In various embodiments, the second micro-controller is further coupled to a sensor 99 being placed in the air pump, or along the air pathway to the inlets of the inflatable air bladders. The sensor 99 is configured to detect the pressure of the compressed air being supplied to the inflatable bladders. The detected air pressure is transmitted back to the second micro-controller 83, such that a precise pressure control can be achieved by the second micro-controller 83.

The precise pressure control can be achieved using feedback control involving a proportional-integral-derivative (PID) control algorithm or other variants of the PID, where applicable. Referring to the PID control algorithm, it is a control loop feedback mechanism, whereby an accurate and responsive correction is applied to meet a pressure set-point as specified by the pressure redistribution commands.

In an embodiment, the second micro-controller 83 controls the fluid supply driver 85 and the thus also the operation of the air pump 98 by applying the PID control algorithm. The sensor 99 reads the air pressure and feeds the information back to the second micro-controller 83 to complete the PID control loop. Advantageously, the PID algorithm restores the actual air pressure supplied to different inflatable bladders 20 to the desired air pressure level in an optimum way, with minimum delay and minimal or no overshoot.

In the manner as described above, the pressure relief mattress 10 is able to use the pressure sensor pad 30 to sense the pressure distributed on different parts of the subject, identify high-pressure zones, compute a pressure redistribution map and send the information to the pressure-control electronic unit 35 for controlling the operation of the plurality of inflatable bladders 20.

The pressure-control electronic unit 35 interprets the pressure distribution commands, performs a precise feedback control to achieve the desired pressure, and activates different solenoid valves 95 to select and pressurise different inflatable bladders 20 to the desired pressure level. Thus, the pressure relief mattress 10 is able to automatically sense pressure on the subject and automatically redistributes the pressure to eliminate high pressure regions where possible. In practice, the pressure exerted on different parts of the subject is controlled to be below 32 mmHg. By keeping track of time, the smart mattress is able to periodically change the pressure distribution so that no part of the body experiences excessive prolonged low blood flow. The risk of developing pressure ulcer is substantially reduced, as adequate blood perfusion for all parts of the body is ensured.

The layout of various electronic components of the pressure relief mattress 10 is illustrated in FIG. 4 by way of an example. It should be understood that other arrangements of the electronic components are also contemplated, for forming an electrically operable pressure relief mattress 10.

In various embodiments, the pressure-sensing electronic unit 33 and the pressure-control electronic unit 35 can be integrated wholly or in part, into one electronic unit. The integrated electronic unit operates to perform the functions of both the pressure-sensing electronic unit 33 and the pressure-control electronic unit 35.

In some embodiments, the first micro-controller 71 of the pressure-sensing electronic unit 33 and the second micro-controller 83 of the pressure-control electronic unit 35 can be integrated wholly or in part, into a controller module. The controller module can include one or more micro-controllers, which are configured to perform the same or similar functions as the first micro-controller 71 and/or the second micro-controller 83.

In various embodiments, the pressure sensor pad 30 is further configured to communicate with an external computing device 47 for monitoring the measurement result from the pressure relief mattress 10.

Figure 5:
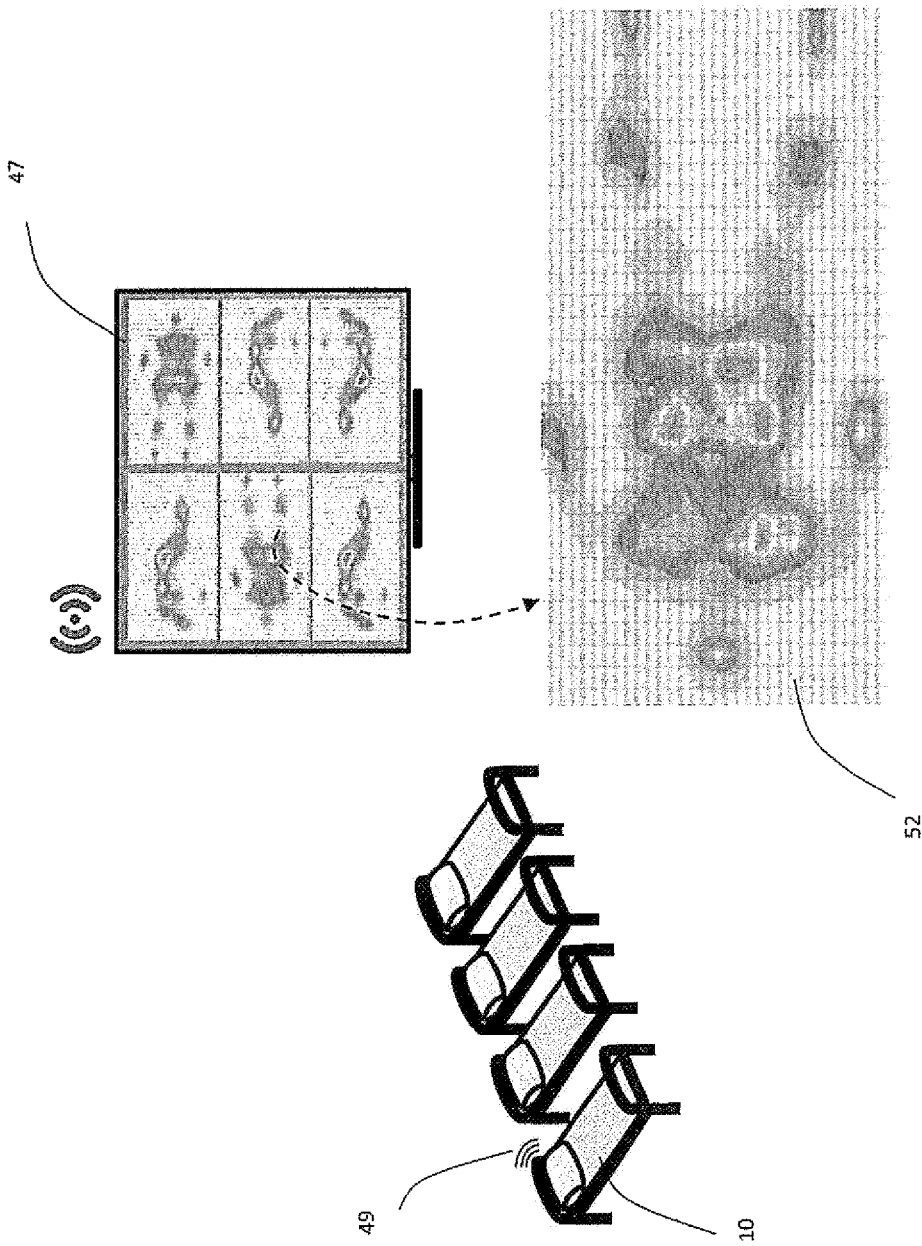
FIG. 5 illustrates an external computing device in communication with the pressure relief mattress of FIG. 1 and/or FIG. 2.

According to an embodiment as shown in FIG. 5, the pressure sensor pad 30 is configured to communicate with the external computing device 47 via a wireless transmission unit 49. The wireless transmission unit 49 is connected to the first micro-controller 71 of the pressure-sensing electronic unit 33 via the first serial communication interface 79. The wireless transmission unit 49 can include one or more wireless transceivers configured to transmit data signals to the external computing device using different types of communication, for example, WiFi and Bluetooth. It is understood that other types of transmission means and different wireless communication protocols are also contemplated, according to requirements.

In a further embodiment, the wireless transmission unit 49 of the pressure relief mattress includes a ZIGBEE transceiver 62 which links up with a wireless mesh network 56.

The external computing device 47 is configured for monitoring the pressure profile of a subject. Reference is made to FIG. 5, showing an illustrative representation of how a pressure distribution map 49 obtained by the pressure relief mattress can be displayed by the coupled external computing device 47. The external computing device 47 includes a display screen, with a matrix of pixels, with each pixel or group of pixels representing a pressure sensor cell on the pressure sensor pad. The pressure detected by each pressure sensor cell is represented by a visual indication. A grayscale may be used such that higher pressures are indicated by different shades, darker grays, for example. Alternatively, or additionally, colors may be used, for example indicating high pressure formed between a subject's body and the surface on which the subject rests by displaying the pixel in a distinctive color, such as red. Likewise, pixels representing sensors which detect low pressure or no pressure at all may be presented in other colors such as yellow, green, blue or black. It is understood that other colors or combinations are also contemplated for the display screen. Additionally, the display screen can be configured to show the pressure distribution for a subject resting on the pressure relief mattress 10, measured at various timings while the subject has changed his/her body positions, as illustrated in FIG. 5.

Using an external computing device 47 provides the benefits of allowing more flexibility for the caregiver to monitor the pressure profile of a subject user resting on the pressure relief mattress 10. For example, it is possible to monitor the subject user's condition from a distance and in real time or near real time.

In various embodiments, the external computing device 47 is also configured for storing information related to the pressure relief mattress 10 and related to the subject user using the pressure relief mattress 10, such as identification data of the subject user and/or a serial number assigned to the pressure relief mattress 10. The external computing device 47 is capable of displaying such information related to the subject user and the pressure relief mattress to a caregiver together with the subject user's body pressure profile. The external computing device 47 is also capable of communicating such information to a computer server or to another computing device.

In various embodiments, the external computing device 47 further includes a control interface being configured to receive a command from the caregiver and transmit the command to the pressure relief mattress for putting the pressure relief mattress 10 in various operational modes. For example, the caregiver can set the pressure relief mattress to measure the pressure distribution of the subject user at different time intervals, such as every five minutes or less, based on the condition or a medical record of the subject user. The caregiver can also enter commands from the external computing device 47 to switch off the pressure relief mattress 10 or put the pressure relief mattress 10 in a power-saving mode.

In various embodiments, the external computing device 47 is configured to allow the caregiver to select from a list of pre-stored pressure relief operational modes according to needs. The list of pre-stored pressure relief operational modes can be activated after the high-pressure points or high-pressure regions on the subject's body have been eliminated, for example, after the pressure relief mattress 10 performs automatic pressure redistribution. In various embodiments, the list of operational modes can include a static low-pressure body support mode, an alternate-pressure body support mode, and a dynamic-pressure body support mode.

When the pressure relief mattress 10 is set to operate at the static low-pressure body support mode, the inflatable bladders 20 are configured to support the subject user at a constant pressure Level for a pre-determined or user-specified period of time, thereby providing a static body support pattern for the subject user. In the static low-pressure body support mode, the static pressure exerted on the subject user is controlled below a pre-determined threshold pressure level, or within a pre-determined range of pressure level.

When the pressure relief mattress 10 is set to an alternate pressure body support mode, the inflatable bladders 20 are configured to support neighbouring zones of the body of the subject user with different pressure levels, which alternate periodically with pre-determined or user-specified time intervals, for example, every 5 to 10 minutes. In the alternate pressure body support mode, the pressure exerted on the neighbouring zones of the subject user is controlled below a pre-determined threshold pressure level, or within a pre-determined range of pressure level.

When the pressure relief mattress 10 is set to operate at the dynamic pressure body support mode, the inflatable bladders 20 are configured to provide slow travelling wave of low-pressure support. The dynamic pressure body support mode promotes relief of blood congestion in tissues under pressure by assisting flow of venous blood and flow of lymphatic fluid within tissue into veins. Similarly, the dynamic pressure exerted on the subject user is always controlled below a pre-determined threshold pressure level, or within a pre-determined range of pressure level.

It is within the scope of the disclosure of the subject invention that other operational modes of the pressure relief mattress 10, as required in the various medical settings, can also be achieved by configuring the external computing device 47 or a readable computer program on the external computing device 47 to execute the different commands entered by a caregiver.

In various embodiments, the external computing device 47 additionally provides a notification means to send alerts to the caregiver. The alert includes but is not limited to an audio alert, visual alert, electronic text alert, electronic mail alert, vibrating alert and/or any combinations thereof. The notification means can be activated in various settings, such as when high pressure regions on the subject user are detected or when human intervention is still required to adjust the body position of the subject user after the pressure relief mattress 10 performs automatic pressure redistribution.

Furthermore, the external computing device 47 can be configured to activate the notification means by using a timer to send a notification to the caregiver at a pre-determined time interval.

It is within the scope of the present disclosure that the pressure sensor pad may be implemented by other suitable means, other than forming capacitance cells using conductive fabric strips and a dielectric substrate as described in this patent disclosure. In various embodiments, the pressure sensor pad includes a matrix of pressure sensor cells formed by using stretch-sensitive fabric, piezo-resistive fabric, force sensors, and/or a combination thereof.

In another aspect, the invention relates to a system 60 using a plurality of the pressure relief mattresses 10 of FIG. 1 or FIG. 2 for managing body pressure distribution of one or more subjects. The system 60 is also referred to as a body pressure management system 60. Exemplary, non-limiting embodiments of the system 60 is described as follows.

In various embodiments, the body pressure management system 60 includes a plurality of the pressure relief mattresses 10 as described in the present disclosure, and at least one external computing device 47. Each pressure relief mattress 10 is in communication with the external computing device 47, such that the external computing device 47 is operable to display pressure measurement results from one or more of the pressure relief mattresses 10 to a caregiver. The external computing device 47 is also configured for the caregiver to enter commands to control the operation of one or more of the pressure relief mattresses 10.

Figure 6:
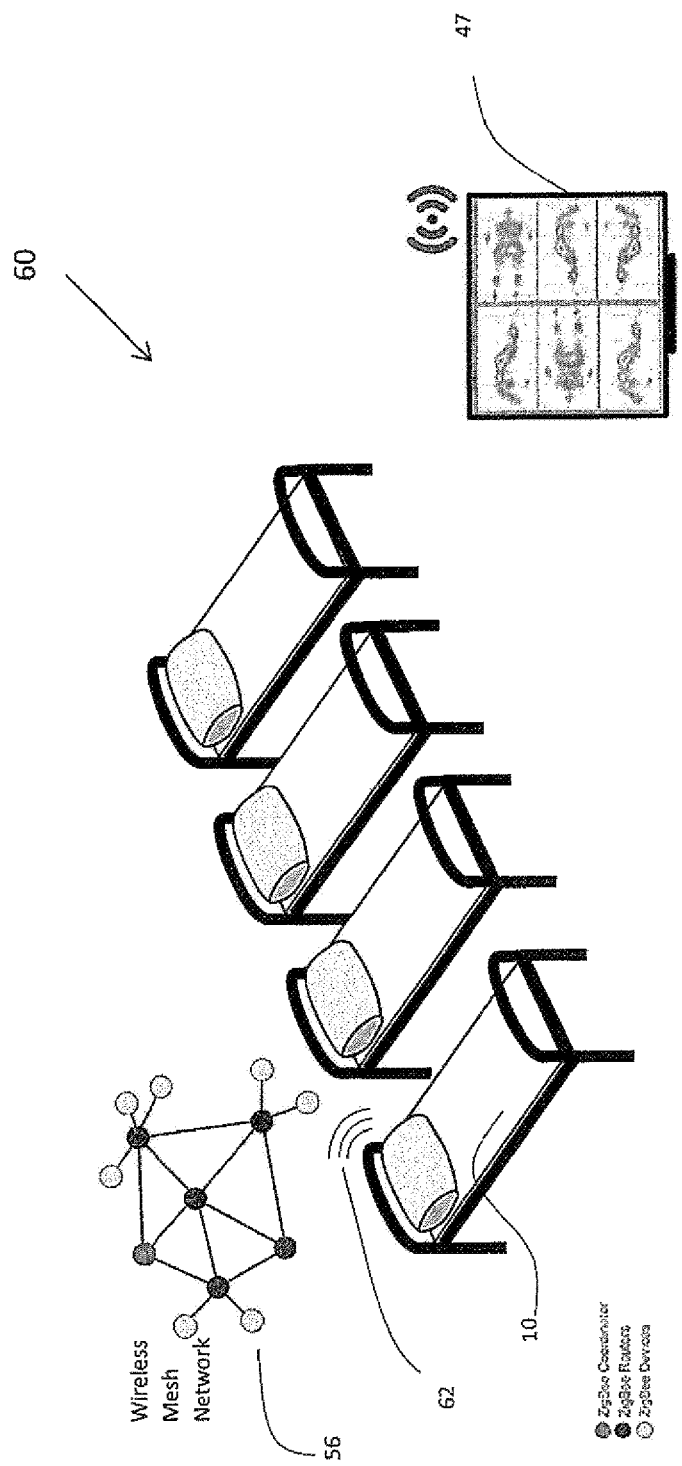
FIG. 6 illustrates a system using a plurality of the pressure relief mattress of FIG. 1 and/or FIG. 2 for managing body pressure of more than one subject users.

In accordance to an embodiment as shown in FIG. 6, each pressure relief mattress 10 of the system 60 includes a transceiver 62 using ZIGBEE communication protocol, which links up with a wireless mesh network 56. The wireless mesh network 56 includes a ZIGBEE coordinator/controller which forms the root of the network tree, one or more Z1GBEE routers acting as relay points to pass on data, and one or more ZIGBEE end devices corresponding to the pressure relief mattresses 10. It is understood that various number of Z1GBEE routers and ZIGBEE end devices can be used to form the wireless mesh network according to different needs.

The pressure relief mattresses 10 in the body management system 60 transmits signals to and received signals from at least one external computing device 47 via the ZIGBEE wireless mesh network 56.

The use of the wireless mesh network 56 provides for simple installation and less expensive and low power-consuming solution to establish effective communication between the pressure relief mattresses 10 of the body pressure management system 60 and also with the external computing devices 47. In hospital settings, the mattresses are usually placed in different sections of wards. Using the system as described, the caregiver can remotely monitor the measurement results from multiple mattresses and control the operation of multiple mattresses centrally from one external computing device 47. Similarly, more than one external computing devices 47 placed at different locations can be linked to the wireless mesh network, allowing a caregiver to select any one of the external computing devices 47 to monitor and control the pressure relief mattresses 10, according to his or her needs.

As such, the caregiver is allowed more flexibility to control multiple pressure relief mattresses 10 for managing the body pressure of multiple subjects or users. Advantageously, the body pressure management system 60 is more efficient and less labour-intensive as compared to the prior art solutions, whereby the human intervention required to adjust the body position of the patients can be performed in a timely manner by any caregiver who is in the neighbourhood of a network-linked external computing device 47 at that time.

Figure 7:
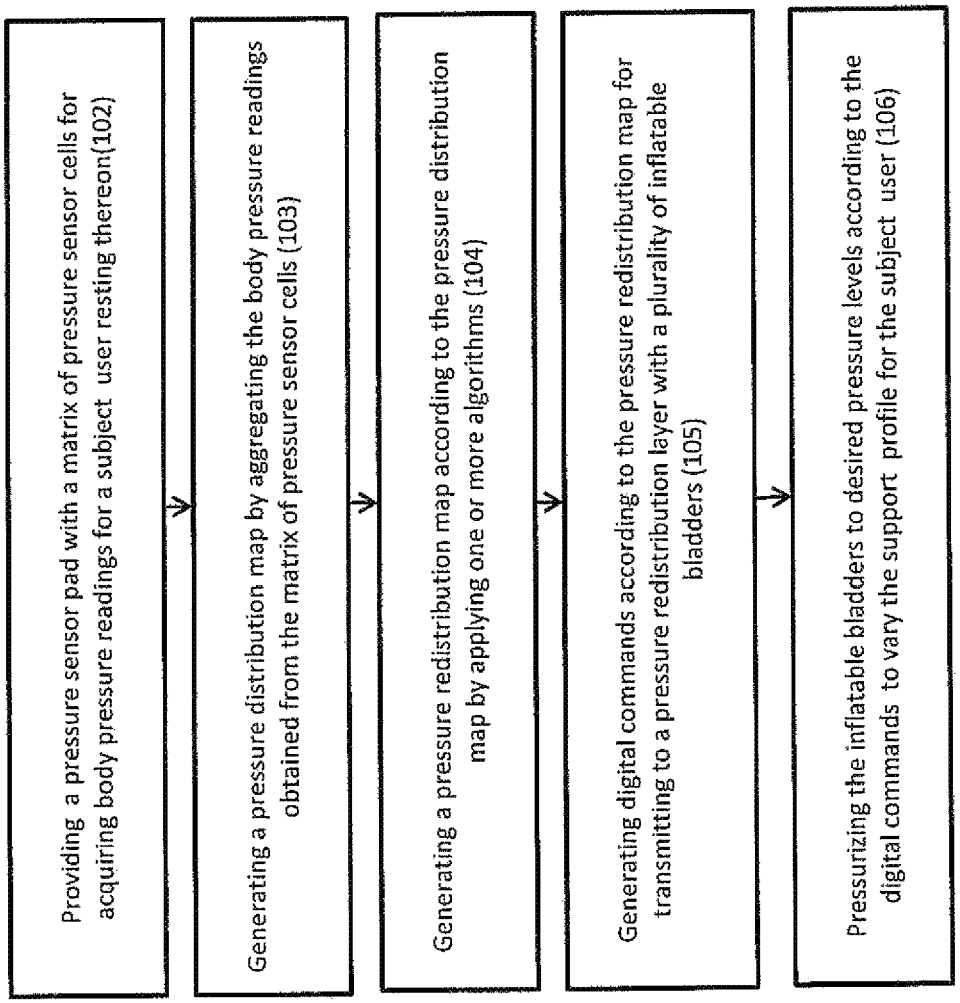
FIG. 7 illustrates a method of managing a body pressure of a subject user.

In another aspect, the invention also relates to a method of managing a body pressure of a subject. Reference is made to FIG. 7, showing a flow diagram which provides a representative example of the method.

In a method step 102, a pressure sensor pad 30 having a matrix of pressure sensor cells 36 is provided for acquiring body pressure of a subject resting thereon. The measurement result from different pressure sensor cells 36 indicates the body pressure at different parts of the subject user.

In a method step 103, a pressure distribution map 52 is generated by aggregating the body pressure measurement results from the different pressure sensor cells 36.

In a method step 104, a pressure redistribution map 53 is generated according to the pressure distribution map 52 by applying one or more algorithms. The one or more algorithms involve identifying regions of high pressure by aggregating readings of pressure above a threshold value by their spatial locations and subsequently generating the pressure redistribution map 53. The pressure level at high-pressure regions as deduced from the pressure distribution map 52 is reduced on the pressure redistribution map 53.

In a method step 105, digital commands are generated according to the pressure redistribution map 53, and are subsequently transmitted to a pressure redistribution layer 26 underneath the pressure sensor pad. The pressure redistribution layer 26 includes a plurality of inflatable bladders 20 capable of being individually pressurized to different pressure levels for adjusting the body-weight support of the subject user lying thereon.

In a method step of 106, the pressure level in one or more of the inflatable bladders 20 are adjusted to a desired pressure level according to the digital commands.

Consequently, the pressure exerted on different parts of the subject is adjusted in an intelligent manner and high-pressure regions can be eliminated automatically according to real-time pressure measurements.

Figure 8:
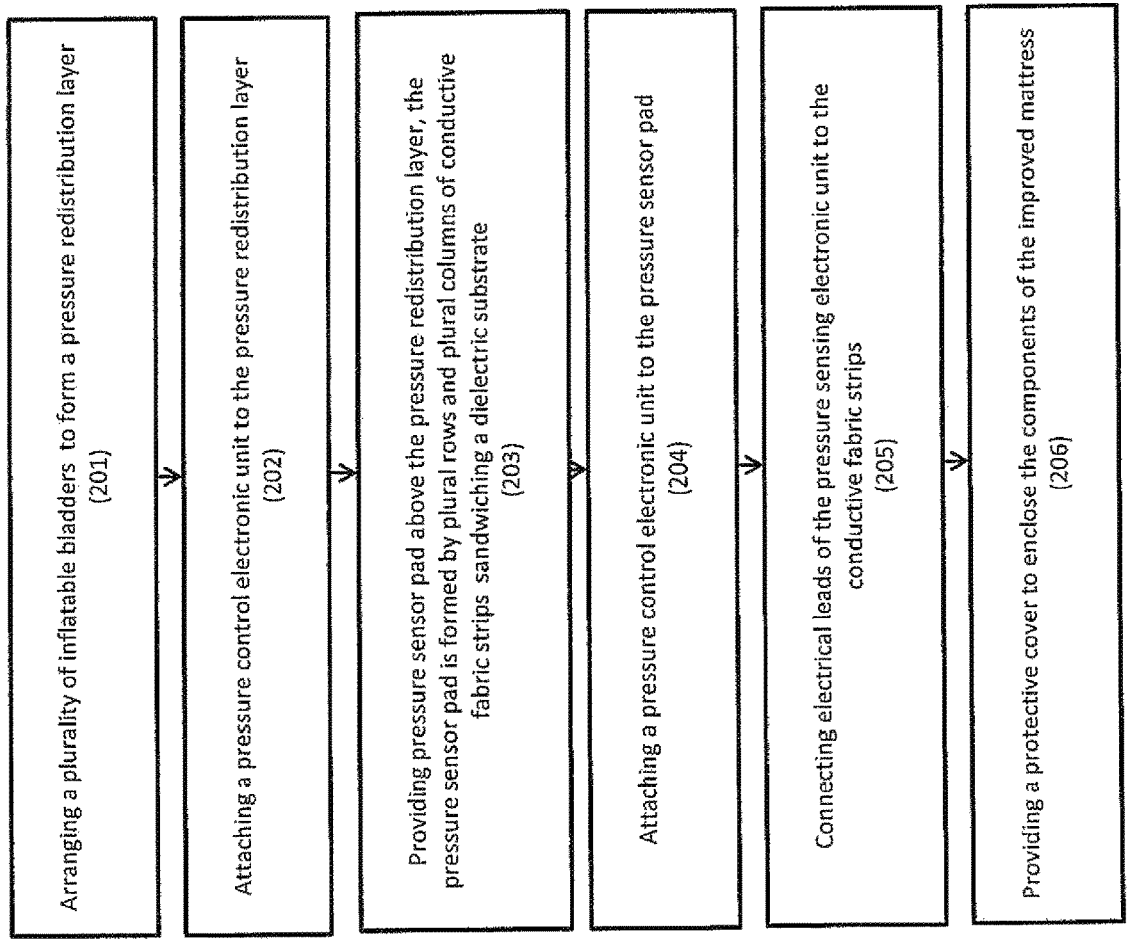
FIG. 8 illustrates a method of producing the pressure relief mattress of FIG. 1 and/or FIG. 2.

In another aspect, the invention relates to a method of producing a pressure relief mattress, as illustrated in FIG. 8.

In a method step of 201, a plurality of inflatable bladders 20 are provided and are arranged to form a pressure redistribution layer 26. An illustrative representation of the arrangement of the inflatable bladders 20 is shown in FIG. 1.

In a method step of 202, a pressure-control electronic unit 35 is provided. The pressure-control electronic unit 35 is attached to the pressure redistribution layer 26.

In a method step of 203, a pressure sensor pad 30 is provided above the pressure redistribution layer 26. The pressure sensor pad 30 can be formed by providing a compressible dielectric substrate 39, providing a plural rows of conductive fabric strips 37 on one surface of the dielectric substrate 39, providing a plural columns of conductive fabric strips 38 on an opposite surface of the dielectric substrate 39. The intersections 41 of the conductive fabric strips 37, 38, which are separated by the compressible dielectric substrate 39, form the matrix of pressure sensor cells 30.

The conductive fabric strips 37, 38 can be affixed on the surfaces of the dielectric substrate 39 using adhesive epoxy, by sewing, and/or a combination thereof, or by some other means, such that the conductive fabric strips 37, 38 do not fall off from the dielectric substrate 40 due to an external force.

In a method step of 204, a pressure-sensing electronic unit 33 is provided. The pressure-sensing electronic unit 33 is affixed to the pressure sensor pad 30.

In a method step of 205, electrical leads of the pressure-sensing electronic unit 33 are connected under software control to the plural rows and plural columns of conductive fabric strips 37, 38, such that the pressure-sensing electronic unit 33 is operatively connected to the pressure sensor pad 30.

In a further method step of 206, a protective cover 10a is provided to enclose the components of the pressure relief mattress. In various embodiments, the protective cover 10a can be liquid impermeable to protect the components embedded in the pressure relief mattress from a liquid. In a further embodiment, the material of the protective cover 10a is a breathable but liquid-impermeable material. In other words, the material of the protective cover 10a is pervious to a gas such as water vapour, but is impervious to various types of liquid.

A method of connecting electrical leads of the pressure-sensing electronic unit to the conductive fabric strips is now described.

In a first method step, a layer of soldering flux is provided on the conductive fabric strips, at selected locations where the electrical leads will be bonded onto.

In a subsequent method step, a pre-determined temperature profile is applied to the soldering flux layer for a pre-determined time period. The soldering flux is heated in a controlled manner and melts due the temperature applied.

In a last method step, electrical leads of the pressure-sensing electronic unit are placed on the melted soldering flux. As the layer of soldering flux cools down and solidifies, a plurality of electrical connections are formed between one or more of the electrical leads and one or more of the conductive fabric strips.

The pre-determined temperature profile and the pre-determined time period for heating up the soldering flux layer is optimized such that a substantially strong adhesion is achieved between the conductive fabric strips and the electrical leads of the pressure-sensing electronic unit. The temperature and the heating time is also controlled to avoid overheating the conductive fabric strips, which would cause the conductive fabric strips to melt or would otherwise compromise the electrical properties of the conductive fabric strips. Further, the electrical connection formed in this manner has a relatively low electrical resistance value. When in use, electrical losses or heat generated due to the electrical resistance at the plurality of electrical connections are substantially reduced. Advantageously, longevity and electrical safety of the pressure relief mattress 10 are improved.

In another aspect, the invention also relates to a control system for managing a body pressure of at least one subject.

The control system comprises one or more pressure redistribution layers. The one or more pressure redistribution layers of the control system are similar to the pressure redistribution layer 26 of the pressure relief mattress 10 of FIG. 1 to FIG. 4. Similar parts/similar electronic circuitry in the pressure redistribution layer 26 of the control system and of the pressure relief mattress 10 have the same or similar reference numbers. The description of pressure redistribution layer 26 of FIG. 1 to FIG. 4 also applies to pressure redistribution layer 26 of the body pressure control system.

In various embodiments, each one of the pressure redistribution layer 26 comprises a plurality of inflatable bladders 20, and a pressure-control electronic unit 35. In various embodiments, the pressure-control electronic unit 35 comprises a communication module being configured to receive a pressure measurement result from a pressure sensor layer, and a controller module being operatively connected to one of more of the inflatable bladders 20. By way of example, the communication module can include at least one serial communication interface 92, which is adapted to receive the pressure measurement result from at least one serial communication interface 79 of one or more pressure sensor layers. It should be understood that other communication means is also contemplated to establish data communication between the pressure redistribution layer 26 and one or more of the pressure sensor layers.

In various embodiments, the controller module of pressure control electronic unit includes at least one micro-controller. The controller module or the micro-controller, the communication module or the serial communication interface 79, and the other parts of the pressure-control electronic unit 35 are arranged in the same or in a similar manner as in the pressure-control electronic unit 35 of FIG. 4.

In use, the controller module receives the pressure measurement result from the communication module, identifies one or more high-pressure regions according to the pressure measurement result, and subsequently generates one or more command streams for lowering the pressure at the identified high-pressure regions by adjusting pressure level in one or more of the inflatable bladders 20. In various embodiments, the pressure measurement result received from the pressure sensor layer is in the form of a pressure distribution map 52. The controller module operates to perform digital signal processing to extract a plurality of strategic measurement parameters from the pressure distribution map 52. One or more algorithms are applied on the measurement parameters to compute a pressure redistribution map 53. In various embodiments, the one or more algorithms involve identifying high-pressure regions by aggregating readings of pressure above a threshold value by their spatial locations and subsequently generating the pressure redistribution map 53. The pressure level at high-pressure regions as deduced from the pressure distribution map 52 is reduced on the pressure redistribution map 53. The pressure redistribution map 53 is subsequently converted into a command stream by the controller module to adjust the pressure level in one or more of the inflatable bladders 20.

In some embodiments, the control system comprises a plurality of the pressure redistribution layers 26. The communication modules of the plurality of pressure redistribution layers 26 are configured to put the plurality redistribution layers 26 in communication with each other via a wireless mesh network. In some embodiments, the wireless mesh network uses ZIGBEE wireless communication protocol.

In some embodiments, the control system is arranged in communication with an external computing device 47 for switching between a plurality of operational modes of one or more of the pressure redistribution layers 26. The external computing device 47 is configured in the same or in a similar manner as the external computing device 47 of FIGS. 5 and 6. The description of the external computing device 47 of FIGS. 5 and 6 also applies to the external computing device 47 connected to the pressure distribution layers 26 of the body pressure control system.

In various embodiments, the external computing device 47 is configured to allow the caregiver to select from a list of pre-stored pressure relief operational modes according to needs. The list of pre-stored pressure relief operational modes can be activated after the high-pressure points or high-pressure regions on the subject's body have been eliminated. In various embodiments, the list of operational modes can include a static low-pressure body support mode, an alternate-pressure body support mode, and a dynamic-pressure body support mode. The pressure redistribution layer 26 of the body pressure control system operates in the same or in a similar manner as the pressure relief mattress 10 under the different operational modes. The description of the different operational modes of the pressure relief mattress 10, such as a static low-pressure body support mode, an alternate-pressure body support mode, and a dynamic-pressure body support mode, also applies to the pressure redistribution layer 26 of the body pressure control system.

In various embodiments, the control system includes a notification means for providing an alert to the caregiver. The alert includes but is not limited to an audio alert, visual alert, electronic text alert, electronic mail alert, vibrating alert and/or any combinations thereof. In some embodiments, the notification means is configured to provide a notification to adjust the pressure of at least one of the plurality of inflatable bladders 20.

In some embodiments, the control system further includes a timer, wherein the pressure redistribution layer 26 adjusts the pressure of at least one of the inflatable bladders 20 at pre-determined time intervals.

It will be apparent that various other modifications and adaptations of the invention will be apparent to the person skilled in the art after reading the foregoing disclosure without departing from the spirit and scope of the invention. It is intended that all such modifications and adaptations come within the scope of the appended claims.

Further, it is to be appreciated that features from various embodiment(s), may be combined to form one or more additional embodiments.

REFERENCE 10 pressure relief mattress
10a protective cover
20 inflatable bladders
26 pressure redistribution layer
30 pressure sensor pad
33 pressure-sensing electronic unit
35 pressure-control electronic unit
36 pressure sensor cell
37 conductive fabric strip
38 conductive fabric strip
39 dielectric substrate
41 intersection of conductive fabric strips
47 external computer device
49 wireless transmission unit
51 transceiver
52 pressure distribution map
53 pressure redistribution map
56 wireless mesh network
60 body pressure management system
62 ZIGBEE transceiver
71 microcontroller
74 multiplexed capacitive sense circuit 76 signal conditioning circuit
79 serial communication interface
83 microcontroller
85 fluid supply driver circuit
89 solenoid valve driver circuit
92 serial communication interface
102 method step
103 method step
104 method step
105 method step
106 method step
201 method step
202 method step
203 method step
204 method step
205 method step
206 method step

The invention claimed is:

1. A pressure-relief mattress comprising:
a plurality of inflatable bladders;
a pressure sensor pad arranged to detect pressure exerted on a subject, the pressure sensor pad comprising:
a dielectric substrate, plural rows of flexible conducting strips disposed on a first surface of the dielectric substrate, and plural columns of flexible conducting strips disposed on a second surface of the dielectric substrate, the plural rows and columns of flexible conducting strips overlapping at a plurality of intersections to form a matrix of pressure sensor cells;
a pressure-sensing electronic unit electrically connected with the matrix of pressure sensor cells, the pressure-sensing electronic unit being configured to selectively drive one or more of the pressure sensor cells for generating a pressure measurement result; and
a pressure-control electronic unit communicatively connected with the pres sure-sensing electronic unit, the pressure-control electronic unit being configured to control operation of one or more of the inflatable bladders according to the pressure measurement result;
wherein the pressure-sensing electronic unit is configured to eliminate interfering signals from neighbouring said pressure sensor cells of the one or more selected said pressure sensor cells, the pressure-sensing electronic unit being configured to selectively drive an active said conducting strip on the first surface of the dielectric substrate with an alternating voltage with reference to a corresponding sensing said conducting strip on the second surface of the dielectric substrate, and to measure a capacitive current from the sensing said conducting strip for generating the pressure measurement result, the pressure-sensing electronic unit being adapted to control neighbouring said conducting strips of the active said conducting strip on the first surface and the sensing said conducting strip on the second surface at a same voltage level.

2. The pressure relief mattress according to claim 1, wherein the pressure-sensing electronic unit is further configured to generate a pressure redistribution map based on the pressure measurement result, and the pressure-control electronic unit is configured to adjust a pressure level of one or more of the inflatable bladders to a desired pressure level based on the pressure redistribution map.

3. The pressure relief mattress according to claim 1, wherein the dielectric substrate is made of a compressible dielectric material.

4. The pressure relief mattress according to claim 3, wherein the compressible dielectric material is a polymeric foam.

5. The pressure relief mattress according to claim 1, wherein the pressure sensor pad comprises 120 to 650 pressure sensor cells.

6. The pressure relief mattress according to claim 1, wherein the pressure relief mattress further comprises at least one fluid supply being operatively coupled to the inflatable bladders and being operatively connected with the pressure-control electronic unit.

7. The pressure relief mattress according to claim 1, wherein the pressure-sensing electronic unit is configured to control the pressure sensor cells using drive signals of a predetermined frequency range.

8. The pressure relief mattress according to claim 7, wherein the frequency of the drive signals used by the pressure-sensing electronic unit to control the pressure sensor cells is in the range of 20 kHz to 200 kHz.

9. The pressure relief mattress according to claim 1, wherein the pressure-sensing electronic unit is configured to process electrical signals of a predetermined frequency range from the pressure sensor cells.

10. The pressure relief mattress according to claim 9, wherein the frequency of the electrical signals from the pressure sensor cells is in the range of 20 kHz to 200 kHz.

11. The pressure relief mattress according to claim 1, wherein the pressure-sensing electronic unit comprises one or more of the following: a) a sense amplifier for amplifying the electrical signals from the pressure sensor cells; a modulator for regulating a waveform of the drive signals and of the electrical signals.

12. The pressure relief mattress according to claim 1, wherein the pressure sensor pad is configured to communicate with an external computing device.

13. The pressure relief mattress according to claim 12, wherein the pressure sensor pad is configured to communicate with the external computing device via a wireless transmission unit.

14. The pressure relief mattress according to claim 13, wherein the wireless transmission unit comprises one or more of the following: -at least one Bluetooth transceiver, or at least one ZIGBEE transceiver.

15. The pressure relief mattress according to claim 12, wherein the external computing device comprises a display unit, the display unit being configured to display the pressure measurement result in the form of a body pressure distribution map.

16. The pressure relief mattress according claim 12, wherein the external computing device comprises a control interface, the control interface being configured to switch between a plurality of operational modes.

17. The pressure relief mattress according to claim 16, wherein the plurality of operational modes comprises a static low-pressure body support mode, an alternate-pressure body support mode, and a dynamic-pressure body support mode.

18. The pressure relief mattress according to claim 12, further comprising a notification means for providing an alert to a caregiver.

19. The pressure relief mattress according to claim 18, wherein the notification means is configured to provide a notification to adjust the pressure of at least one of the plurality of inflatable bladders.

20. The pressure relief mattress according to claim 19, further comprising a timer, wherein the pressure relief mattress adjusts the pressure of at least one of the plurality of inflatable bladders at pre-determined time intervals.

21. A system for managing a body pressure of one or more subjects comprising:
one or more pressure relief mattresses according to claim 1, and
one or more external computing devices in communication with one or more of the pressure relief mattresses,
wherein the external computing device is configured to receive a pressure measurement result from one or more of the pressure relief mattresses for monitoring the pressure measurement result and for putting one or more of the pressure relief mattresses in various operational modes.

22. The system according to claim 21, wherein the one or more pressure relief mattresses are arranged in signal communication with each other via a wireless mesh network.

23. The system according to claim 22, wherein the wireless mesh network uses ZIGBEE wireless communication protocol.

24. A control system for managing body pressure of at least one subject, which comprises one or more pressure relief mattresses according to claim 1, wherein
the pressure-control electronic unit comprises a communication module being configured to receive a pressure measurement result from the pressure sensor pad, and a controller module being operatively connected to one or more of the inflatable bladders,
wherein the controller module is configured to identify one or more high-pressure regions according to the pressure measurement result, and generate a pressure redistribution map for lowering a pressure at the identified high-pressure regions, and adjust a pressure level in one or more of the inflatable bladders to a desired pressure level according to the pressure redistribution map.

25. The control system according to claim 24, wherein the one or more pressure relief mattresses are configured to connect with each other via a wireless mesh network.

26. The control system according to claim 25, wherein the wireless mesh network uses ZIGBEE wireless communication protocol.

27. The control system according to claim 24, wherein the control system is arranged in communication with an external computing device for switching between a plurality of operational modes of one or more of the pressure relief mattresses.

28. The control system according to claim 24, further comprising a notification means for providing an alert to the caregiver.

29. The control system according to claim 28, wherein the notification means is configured to provide a notification to adjust the pressure of at least one of the plurality of inflatable bladders.

30. The control system according to claim 29, further comprising a timer, wherein the pressure relief mattress adjusts the pressure of at least one of the plurality of inflatable bladders at pre-determined time intervals.

31. A method of managing a body pressure of a subject lying on a support surface comprising:
measuring the body pressure at a plurality of locations on the support surface by using a pressure sensor pad having a matrix of pressure sensor cells, the pressure sensor pad comprising a dielectric substrate, plural rows of flexible conducting strips disposed on a first surface of the dielectric substrate, and plural columns of flexible conducting strips disposed on a second surface of the dielectric substrate, the plural rows and columns of flexible conducting strips overlapping at a plurality of intersections to form the matrix of pressure sensor cells,
selecting one or more of the pressure sensor cells by a pressure-sensing electronic unit for generating a pressure measurement result,
creating a pressure distribution map according to the body pressure measured at the plurality of locations,
generating a pressure redistribution map according to the pressure distribution map,
generating at least one digital command according to the pressure redistribution map,
transmitting the at least one digital command to a pressure-redistribution layer having a plurality of inflatable bladders, and adjusting a pressure level in one or more inflatable bladders to a desired pressure level according to the at least one digital command,
wherein the pressure-sensing electronic unit is configured to eliminate interfering signals from neighbouring said pressure sensor cells of the one or more selected said pressure sensor cells, the pressure-sensing electronic unit being configured to selectively drive an active said conducting strip on the first surface of the dielectric substrate with an alternating current with reference to a corresponding sensing said conducting strip on the second surface of the dielectric substrate, and to measure a capacitive current from the sensing said conducting strip for generating the pressure measurement result, the pressure-sensing electronic unit being adapted to control neighbouring said conducting strips of the active said conducting strip on the first surface and the sensing said conducting strip on the second surface at a same voltage level.

* * * * *